United States Patent [19]
Ahr

[11] Patent Number: 5,562,651
[45] Date of Patent: Oct. 8, 1996

[54] ABSORBENT ARTICLE WITH ADJUSTABLE UNDERGARMENT PROTECTION SYSTEM

[75] Inventor: Nicholas A. Ahr, Cincinnati, Ohio

[73] Assignee: The Procter & Gamble Company, Cincinnati, Ohio

[21] Appl. No.: 268,694

[22] Filed: Jun. 30, 1994

[51] Int. Cl.⁶ ................................................. A61F 13/15
[52] U.S. Cl. ........................................ 604/387; 604/385.1
[58] Field of Search ............................... 604/385.1, 387, 604/383, 386

[56] References Cited

U.S. PATENT DOCUMENTS

| 4,425,130 | 1/1984 | DesMarais . | |
|---|---|---|---|
| 4,605,405 | 8/1986 | Lassen | 604/389 |
| 4,758,241 | 7/1988 | Papajohn | 604/387 |
| 4,940,462 | 7/1990 | Salerno | 604/387 |
| 5,007,906 | 4/1991 | Osborn, III et al. . | |
| 5,037,418 | 8/1991 | Kons et al. . | |
| 5,087,254 | 2/1992 | Davis et al. . | |
| 5,275,591 | 1/1994 | Mavinkurve | 604/387 |
| 5,507,735 | 4/1996 | Van Iten et al. | 604/385.1 |

FOREIGN PATENT DOCUMENTS

0467184A1  1/1992  European Pat. Off. .

Primary Examiner—John G. Weiss
Assistant Examiner—Mark O. Polutta
Attorney, Agent, or Firm—Edward J. Milbrada; Jeffrey V. Bamber; Steven W. Miller

[57] ABSTRACT

Absorbent articles, particularly sanitary napkins, having longitudinally adjustable flaps are provided. The flaps are connected to the central absorbent body of the article by an extensible means and can be adjusted in the longitudinal direction either by manually positioning the flaps or by using an optional adjustment tab to adjust the position of the flaps. Absorbent articles of the present invention thus provide improved protection to undergarments and improved comfort to a wearer, since the wearer can adjust both the flaps and the central absorbent body of the article in an optimal position for their particular needs.

8 Claims, 3 Drawing Sheets

ABSORBENT ARTICLE WITH ADJUSTABLE UNDERGARMENT PROTECTION SYSTEM

FIELD OF THE INVENTION

The invention disclosed herein relates to disposable absorbent articles, particularly sanitary napkins, and more particularly sanitary napkins with an adjustable undergarment protection system for providing improved protection against soiling.

BACKGROUND OF THE INVENTION

Sanitary napkins and related disposable absorbent articles which provide for the collection of menses and other bodily discharges are well known in the art. It has long been an object of sanitary napkins to readily intercept menses upon discharge from the wearer. Such sanitary napkins typically have a means, such as pressure sensitive adhesive, for affixing the sanitary napkin to the undergarment of a wearer and for maintaining the sanitary napkin in the proper position to intercept the discharged menses.

However, different wearer's needs for protecting undergarments vary. In addition, the wearer's undergarment may not, in fact, move in concert with the wearer's body. Specifically, the crotch of the wearer's undergarment may not be in an optimal position relative to the vaginal opening. Also, as the wearer spreads her legs, walks, sits, etc., the sanitary napkin may not flex and twist with the undergarment-stressing the means for affixing the sanitary napkin to the undergarment of the wearer. In fact, the pressure sensitive adhesive may become detached from the undergarment, further allowing the sanitary napkin to shift from the desired position and registration with resulting loss of protection.

Several attempts in the art have been made to provide a sanitary napkin which may be attached to the undergarment of the wearer and also maintain the constant position with respect to the body of the wearer. For example, U.S. Pat. No. 4,425,130 issued Jan. 10, 1984 to DesMarais discloses a sanitary napkin having decoupled components joined at the transverse edges and U.S. Pat. No. 5,007,906 issued Apr. 16, 1991 to Osborn III, et al. discloses a sanitary napkin with a topsheet and an absorbent core that are decoupled from the backsheet allowing the topsheet and the backsheet to be separated in the Z-direction.

Attempts have also been made to provide sanitary napkins with improved means for protection of a wearer's undergarment. For example U.S. Pat. No. B1 4,589,876 Reexamination Certificate issued Apr. 27, 1993 to Van Tilburg describes a sanitary napkin with flaps that extend laterally from a longitudinal edge of a central absorbent core. The flaps wrap around the crotch portion of the undergarment preventing soiling thereof. U.S. Pat. No. 5,037,418 issued to Kons, et al. on Aug. 6, 1991 discloses an absorbent article designed to be attached to the crotch region of an undergarment. An optionally attachable protective sheet is provided which can wrap the crotch region of the undergarment to prevent staining.

Other attempts have been made to provide sanitary napkins that compensate for pad movement due to wearer motion. Examples include U.S. Pat. No. 4,605,405 issued to Lassen on Aug. 12, 1986 which describes a sanitary napkin with a positioning strap attached to the pad on one end of the strap, means for attaching the strap to the undergarment on the other end of the strap, and a low friction baffle which is said to allow longitudinal sliding of the pad in response to wearer motion. U.S. Pat. No. 4,609,373 issued to Johnson on Sep. 2, 1986 discloses a perineal pad said to limit the range of possible displacement of the pad. The pad has a strip attached to the pad at one end and attachment means at the other end of the strip. The strip is passed through a loop in an undergarment and then attached to the garment facing side of the pad using the attachment means.

However, none of the attempts described hereinabove provides a unitary disposable absorbent article which has an adjustable undergarment protection system which allows a wearer to position the article in an optimal location and attach it to an undergarment in that location so it remains reliably attached there.

It is an object of this invention to provide a sanitary napkin which more readily intercepts menses as it is discharged. Also, it is an object of this invention to provide a sanitary napkin which remains in an optimal location throughout the range of normal movements encountered while the sanitary napkin is worn. Finally, it is an object of this invention to provide a sanitary napkin which allows a wearer to determine what the optimal location is for her particular needs and attach the sanitary napkin in that location.

SUMMARY OF THE INVENTION

The present invention relates to a sanitary napkin that includes a central absorbent body having longitudinal sides and transverse ends that comprises a liquid pervious topsheet, a liquid impervious backsheet, and an absorbent core interposed between the topsheet and backsheet. The sanitary napkin further comprises an adjustable undergarment protection system which preferably comprises a pair of side flaps and a flap connecting member having longitudinal sides and transverse ends with side the flaps extending laterally outward from each longitudinal side of the flap connecting member beyond the longitudinal edges of the central absorbent body. Each flap preferably comprises a liquid pervious topsheet, a liquid impervious backsheet, and an attachment adhesive disposed on the garment facing side of the flap. The adjustable undergarment protection system additionally comprises at least one longitudinally extensible component such as an attachment member joining a transverse end of the flap connecting member with the garment facing side of the backsheet of the central absorbent body.

Sanitary napkins of the present invention allow a user to independently position the central absorbent body and the flaps for maximum comfort and protection. That is, a user can place a sanitary napkin of the present invention in the optimal location for her particular needs and independently adjust the position of the side flaps.

BRIEF DESCRIPTION OF THE DRAWINGS

While the specification concludes with claims particularly pointing out and distinctly claiming the present invention, it is believed the same will be better understood from the following description taken in conjunction with the accompanying drawings wherein like parts are given the same reference numeral, and:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
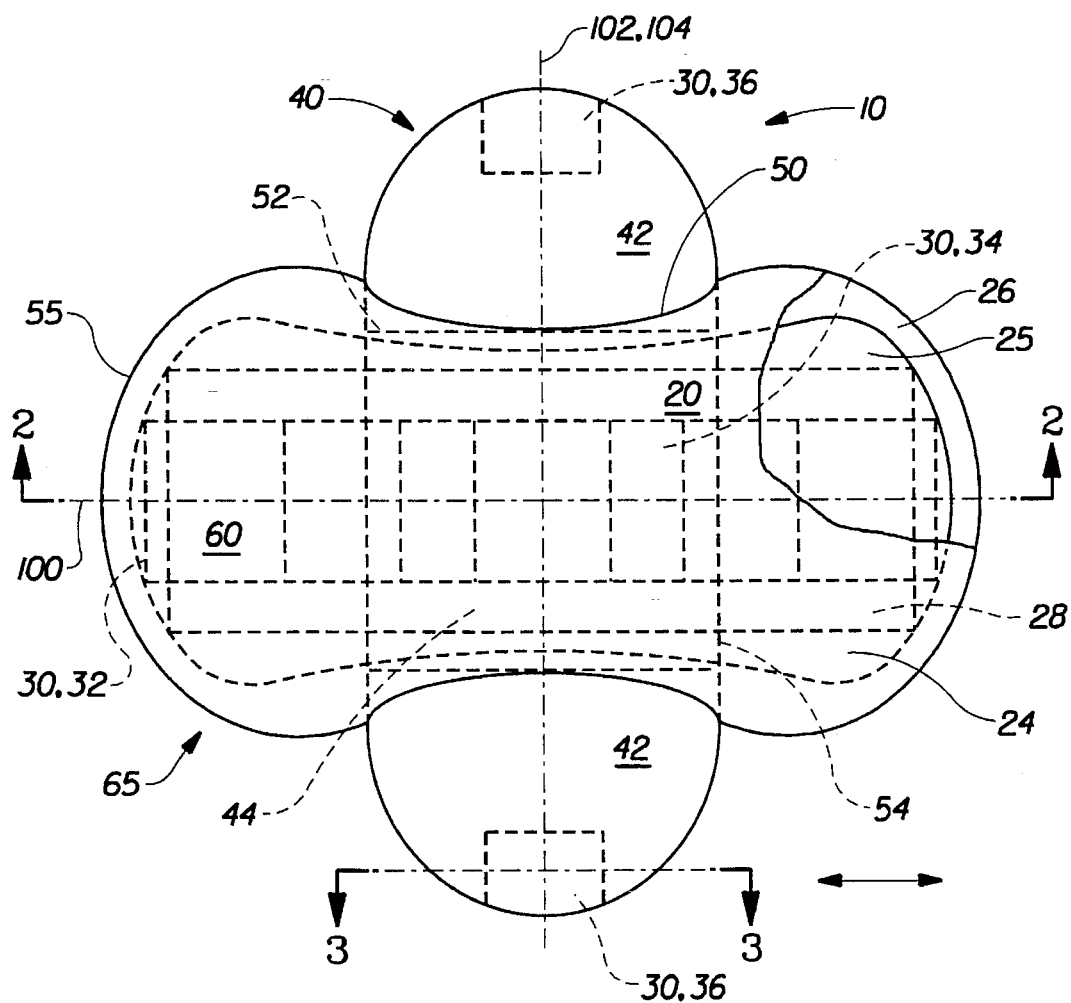
FIG. 1 is a top plan view, partially shown in cutaway, of a sanitary napkin according to the present invention.

A preferred embodiment of a unitary disposable absorbent article of the present invention is the catamenial pad, sanitary napkin 10, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Intelabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

FIG. 1 is a plan view of the sanitary napkin 10 of the present invention in its flat-out state with portions of the structure being cut-away to more clearly show the construction of the sanitary napkin 10 and with the portion of the sanitary napkin 10 which faces or contacts the wearer, oriented towards the viewer. The sanitary napkin 10 has two surfaces, a body-contacting surface 60 or "body surface" and a garment surface 65. The sanitary napkin 10 is shown in FIG. 1 as viewed from its body surface. The body surface is intended to be worn adjacent to the body of the wearer while the garment surface is on the opposite side and is intended to be placed adjacent to the wearer's undergarments when the sanitary napkin 10 is worn. As shown in FIG. 1, the sanitary napkin 10 preferably comprises a central absorbent body 20 and an adjustable undergarment protection system 40.

The central absorbent body 20 comprises a liquid pervious topsheet 24, a liquid impervious backsheet 26 joined with the topsheet 24, and an absorbent core 28 positioned between the top sheet 24 and the backsheet 26. FIG. 1 also shows that the central absorbent body 20 has a periphery which is defined by the outer edges of the central absorbent body 20 in which the longitudinal edges are designated 50 and the end edges are designated 55. The central absorbent body 20 further has a longitudinal centerline 100 and a transverse centerline 102. The term "longitudinal", as used herein, refers to a line, axis or direction in the plane of the sanitary napkin 10 that is generally aligned with (e.g., approximately parallel to) a vertical plane which bisects a standing wearer into left and right body halves when the sanitary napkin 10 is worn. The terms "transverse" or "lateral" as used herein, are interchangeable, and refer to a line, axis or direction which lies within the plane of the sanitary napkin 10 that is generally perpendicular to the longitudinal direction.

While the topsheet, the backsheet, and the absorbent core may be assembled in a variety of well known configurations (including so called "tube" products), preferred sanitary napkin configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987, U.S. Pat. No. 5,009,653 "Thin, Flexible Sanitary Napkin" issued to Osborn on Apr. 23, 1991, and U.S. Pat. No. 5,308,346 "Elasticized Sanitary Napkin" issued to Sneller, et al. on May 3, 1994. Each of these patents are hereby incorporated herein by reference. FIG. 1 shows a preferred embodiment of the sanitary napkin 10 in which the topsheet 24 and the backsheet 26 have length and width dimensions generally larger than those of the absorbent core 28. The topsheet 24 and the backsheet 26 extend beyond the edges of the absorbent core 28 to thereby form portions of the periphery.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet are non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, the topsheet can be made hydrophilic by treating it with a surfactant such as is described in the above referenced U.S. Pat. Nos. 4,950,254 and 5,009,653 both issued to Osborn, incorporated herein by reference.

The absorbent core 28 may be any absorbent means which is capable of absorbing or retaining liquids (e.g., menses and/or urine). As shown in FIG. 1, the absorbent core 28 has a body surface, a garment surface, side edges, and end edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones or be profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. A preferred embodiment of the absorbent core 28 of the present invention comprises a layer of superabsorbent material disposed between two air laid tissues as described in U.S. Pat. No. 4,950,264 entitled "Thin, Flexible Sanitary Napkin" issued to Osborn on Aug. 21, 1990 and U.S. Pat. No. 5,009,653 entitled "Thin, Flexible Sanitary Napkin" issued to Osborn on Apr. 23, 1991. Each of these patents are incorporated herein by reference.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the sanitary napkin 10 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385. The backsheet is preferably embossed and/or matte finished to provide a more clothlike appearance. Further, the backsheet 26 may permit vapors to escape from the absorbent core 28 (i.e., breathable) while still preventing eradates from passing through the backsheet 26.

The backsheet 26 and the topsheet 24 are positioned adjacent the garment surface and the body surface, respectively, of the absorbent core 28 and are preferably joined thereto and to each other by attachment means (not shown) such as those well known in the art. For example, the backsheet 26 and/or the top sheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

Figure 2:
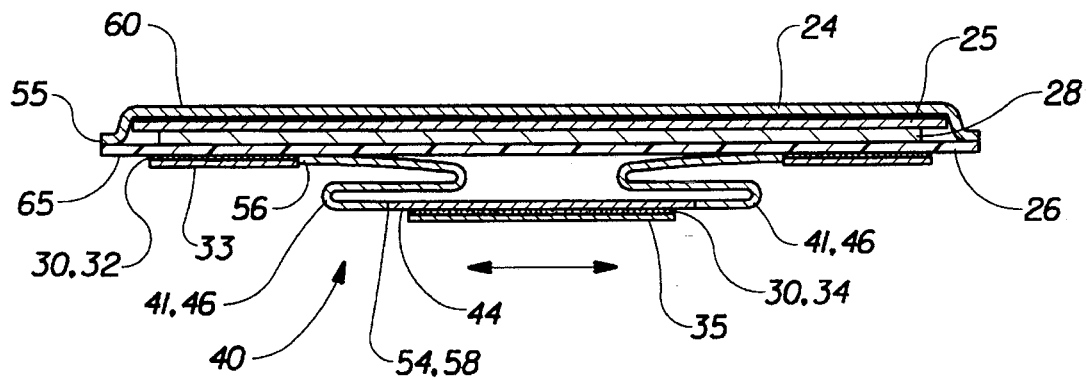
FIG. 2 is a sectional view taken along lines 2—2 of FIG. 1, showing a preferred embodiment of the adjustable undergarment protection system of the present invention.

In the preferred embodiment of the present invention shown in FIGS. 1 and 2, an acquisition component (or components) 25 may either be positioned between the top sheet and the absorbent core, or comprise the bottom surface of a composite topsheet. The acquisition component may serve several functions. These functions include improving wicking of exudates over and into the absorbent core. The improved wicking of exudates is important because it provides a more even distribution of the exudates throughout the absorbent core and allows the sanitary napkin 10 to be made relatively thin. (The wicking referred to herein may encompass the transportation of liquids in one, two, or all directions (i.e., in the x-y plane and/or in the z-direction). The acquisition component may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition component are more fully described in U.S. Pat. Nos. 4,950,264 and 5,009,653 both issued to Osborn, and PCT Patent Publication WO 93/11725 "Absorbent Article Having Fused Layers", issued to Cree, et al. and now pending as U.S. patent application Ser. No. 08/239,084 filed May 6, 1994. Each of these references is incorporated herein by reference. In a preferred embodiment, the acquisition component may be joined with the topsheet by any of the conventional means for joining webs together, most preferably by fusion bonds as is more fully described in the above-referenced Cree et al. patent application.

In use, the sanitary napkin 10 can be held in place by any attachment means 30 well-known for such purposes. Preferably, the sanitary napkin is placed in the user's undergarment or panty and secured thereto by a fastener such as an adhesive. The adhesive provides a means for securing the sanitary napkin in the crotch portion of the undergarment. Thus, a portion or all of the garment surface 65 of the sanitary napkin 10 may be coated with adhesive. For the preferred embodiment of the present invention shown in FIGS. 1–3 and the alternative embodiment shown in FIGS. 4 and 5, these portions are disposed on both the central absorbent body 20 and the undergarment protection system 40 of the sanitary napkin 10. That portion of the adhesive disposed on the central absorbent body is identified as the pad adhesive 32 and that portion disposed on the undergarment protection system is identified as connector adhesive 34 or as flap adhesive 36 depending on which element of the undergarment protection system whereon the adhesive is disposed. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. The pressure-sensitive adhesive is typically covered with a removable release liner in order to keep the adhesive from adhering to a surface other than the crotch portion of the undergarment prior to use. These are identified as the pad release liner 33, the connector release liner 35, and the flap release liner 37 in FIGS. 1–4. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. Suitable release liners are also described in the above-referenced U.S. Pat. No. 4,917,697. The sanitary napkin 10 of the present invention is used by removing the release liner and thereafter placing the sanitary napkin in an undergarment so that the adhesive contacts the undergarment. The adhesive maintains the sanitary napkin in its position within the undergarment during use.

The sanitary napkin of the present invention further comprises an adjustable undergarment protection system 40. In the preferred embodiment shown in FIGS. 1–3, the undergarment protection system comprises two flaps 42; a flap connecting member 44; and two attachment members 46. As can be seen from FIGS. 1 and 2, the flaps 42 can be moved longitudinally relative to the central absorbent body 20 (in the direction shown by the arrows) allowing a wearer to position the pad and independently adjust the flaps for maximum comfort and maximum protection prior to attaching the flaps to her undergarment. The flaps 42 preferably can be adjusted over a range of longitudinal adjustment index from about 5% to about 50%. Flaps that can be adjusted over such a range of longitudinal adjustment index can be optimally positioned relative to the central absorbent body 20 to meet individual wearer needs for comfort and protection. As used herein, the term "longitudinal adjustment index" means the percentage of the longitudinal distance along longitudinal centerline 100 between the central absorbent body transverse centerline 102 and the central absorbent body end edge 55 that the flap transverse centerline 104 can be offset by longitudinal adjustment. For example, if a user of a typical sanitary napkin 10, with a longitudinal length of 23 cm, adjusts the flap 42 so that the flap transverse centerline 104 is offset 5 cm from the central absorbent body transverse centerline 102, the longitudinal adjustment index would be:

$$\text{Longitudinal Adjustment Index} = \frac{5}{\left(\frac{23}{2}\right)} \cdot 100 = 43\%$$

The flaps 42 extend laterally beyond the longitudinal edges 50 of the central absorbent body 20. The flaps 42 are joined to the flap connecting member 44, discussed hereinbelow, at the longitudinal edges 52 of the flap connecting member 44. The flaps are configured to drape over the edges of the wearer's underwear in the crotch region so that the flaps are disposed between the edges of the wearer's underwear and the thighs. The flaps serve at least two purposes. First, the flaps help serve to prevent soiling of the wearer's body and underwear by menstrual fluid, preferably by forming a double wall barrier along the edges of the undergarment. Second, the flaps are preferably provided with a portion of the attachment means 30, the flap adhesive 36, on their garment surface so that the flaps can be folded back under the undergarment and attached to the garment facing side of the undergarment or to each other. In this way, the flaps serve to keep the sanitary napkin properly positioned in the undergarment. The flaps can be constructed of various materials including materials similar to the topsheet, backsheet, tissue, or combination of these materials. A number of sanitary napkins having flaps suitable or adaptable for use with the sanitary napkins of the present invention are disclosed in U.S. Pat. No. 4,687,478 emitted "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

Figure 3:
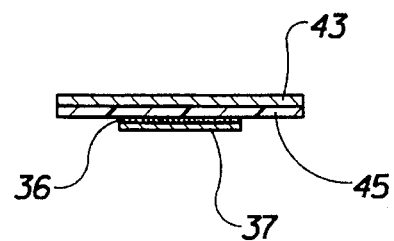
FIG. 3 is a sectional view taken along lines 3—3 of FIG. 1, showing a preferred structure for the flap component of the adjustable undergarment protection system of the present invention.

FIG. 3 shows a preferred embodiment of a flap 42. In this embodiment the flap 42 is a two ply structure. The body contacting ply 43 is made of the same material used for the topsheet 24 and the garment contacting ply 45 is made of the material used for the backsheet 26. This two ply structure has several advantages. The top sheet material will be in contact with a wearer's body during use so the compliant, soft feeling, and non-irritating properties of the topsheet material will contribute to wearer comfort. The liquid impervious property of the backsheet provides additional protection to the wearer's clothing. Disposed on each flap is the flap adhesive 36.

The undergarment protection system 40 preferably further comprises a flap connecting member 44. As can be seen in FIGS. 1 and 2, the flap connecting member 44 joins or bridges the two flaps 42. The flaps extend from the longitudinal sides 52 of the flap connecting member 44. The flap connecting member further comprises transverse ends 54. The flap connecting member is disposed beneath the garment facing surface 65 on the central absorbent body portion of the sanitary napkin 10. That is, the flap connecting member 44 is disposed between the backsheet and a wearer's undergarment. Further, there is a connector adhesive 34 disposed on the flap connecting member 44 allowing a wearer to fix the adjustable undergarment protection system to her undergarment in a preferred location.

The flap connecting member 44 can comprise any thin, flexible material. Examples include woven or nonwoven material, polymeric films such as thermoplastic films of polyethylene or polypropylene, or composite materials such as a film-coated nonwoven material. A preferred material for the present invention is the same polyethylene film used for the backsheet.

It should be understood, however, that in other embodiments, the flaps 42 and the flap connecting member 44 can comprise a single component rather than separate components. In such embodiments, the flap connecting member 44 would simply be a region or an integral portion of this single flap component.

The undergarment protection system 40 of the preferred embodiment shown in FIGS. 1 and 2 still further comprises two attachment members 46. These attachment members 46 join the flap connecting member 44 to the backsheet 26 in a manner which permits the flaps 42 and the flap connecting member 44 to be adjusted longitudinally. The attachment members tie the adjustable undergarment protection system to the central absorbent body in order to form a unitary sanitary napkin 10 in which the key elements comprising the sanitary napkin 10 can be positioned in an optimal location by a wearer without the added complexities of a multi-part article.

In the preferred embodiment of the sanitary napkin 10 shown in FIGS. 1 and 2, a first end 58 of each attachment member 46 is joined to and extends longitudinally from the flap connecting member 44. Preferably, a first end 58 is joined to and extends longitudinally from each of the transverse edges 54 of the flap connecting member 44. The second end 56 of an attachment member 46 is joined to the backsheet 26 at a point intermediate the central absorbent body transverse centerline 102 and the central absorbent body end edge 55. The specific location of the point of joining the attachment member 46 to the backsheet 26 and the longitudinal length of the attachment member 46 is determined by the desired range of longitudinal adjustment index and the size and location of the pad adhesive 32.

The attachment member 46 can be joined to both the flap connecting member 44 and to the backsheet 26 by any means familiar to the art such as a uniform continuous layer of adhesive, a patterned layer of adhesive, or an array of separate lines, spirals, or spots of adhesive. Alternatively, the means may comprise heat bonds, pressure bonds, ultrasonic bonds, dynamic mechanical bonds, or any other suitable attachment means or combinations of these means as are known in the art.

In the embodiment of the present invention shown in FIGS. 1 and 2, each attachment member 46 preferably comprises an adjustment feature 41 or a "means for longitudinally adjusting the flaps". As shown in these figures, the adjustment feature 41 provides the attachment member 46 with at least two transversely oriented folds forming a pleat. That is, each attachment member 46 is z-folded. These folds allow the longitudinal position of the flaps 42 to be varied while the flaps still remain attached to the central absorbent body 20. The adjustment feature 41, however, is not limited to the z-folded attachment member 46 shown in FIGS. 1 and 2. The adjustment feature 41 can comprise any type of structure that permits the flaps to be adjusted longitudinally. For example, the attachment member 46 can be provided with slack, without folding. Or, in another alternative embodiment, the attachment member 46 can comprise an extensible material preferably having a low yield value and a high elongation to break to allow longitudinal adjustment of the undergarment protection system 40. In still further embodiments, the adjustment feature 41 can comprise all or a portion of some other component of the sanitary napkin 10, including, but not limited to the flap connecting member 44, slip element 48 described hereinbelow, or other components of the sanitary napkin 10.

In the embodiment shown in FIGS. 1 and 2, the attachment member 46 can comprise any thin, flexible material. Examples include woven or nonwoven material, polymeric films such as thermoplastic films of polyethylene or polypropylene, or composite materials such as a film-coated nonwoven material. A preferred material for the present invention is the same polyethylene film used for the backsheet.

To use a sanitary napkin 10 of the preferred embodiment shown in FIGS. 1–3, a wearer would first remove the connector release liner 35, position the flap connecting member 44 in the desired location and attach the flap connecting member to her underwear. She would then remove the flap release liner 37 from both portions of flap adhesive 36 and attach the flaps 42 to her undergarment or to each other. Lastly, she would remove the pad release liner 33, position the central absorbent body 20 in her preferred location, and attach it to her undergarment.

Figure 4:
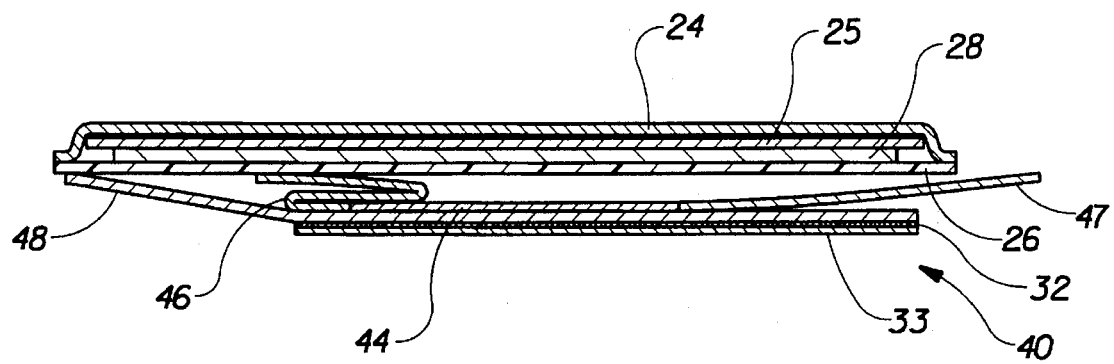
FIG. 4 is a sectional view taken along lines 2—2 of FIG. 1, showing an alternative embodiment of the adjustable undergarment protection system of the present invention.

FIG. 4 shows an alternative embodiment of the present invention. Instead of comprising two attachment members 46, the adjustable undergarment protection system 40 of this embodiment comprises one attachment member 46 and an adjustment tab 47. The adjustment tab 47 provides an alternative means for a wearer to position the flaps 42 in an optimal location. The alternative embodiment of the sanitary napkin 10 shown in FIG. 4 further comprises a slip element 48 that encases the adjustment tab 47. The slip element 48 is provided in the embodiment of FIG. 4 for three reasons: 1) to provide a garment contacting surface wherein the pad adhesive 32 can be disposed, 2) to provide a means for controlling the transverse motion of the adjustment tab 47, and 3) to enable longitudinal adjustment of the flaps 42 after the central absorbent region 20 has been attached to a wearer's undergarment.

To use the adjustment tab 47, a wearer would position the central absorbent body 20 in a preferred location in the crotch area of her undergarment and attach it using the pad adhesive 32. When a wearer grasps the adjustment tab 47 and pulls, the flap connecting member 44 and the attached flaps 42 slide between backsheet 26 and the slip element 48 allowing the wearer to position the flaps 42 in her preferred location for attachment to the undergarment using the flap adhesive 36. Optionally, a patch of adhesive can be disposed on the free end of the adjustment tab 47 allowing it to be attached to the undergarment after the flaps 42 have been positioned.

The adjustment tab 47 can comprise any thin, flexible material. Examples include woven or nonwoven material, polymeric films such as thermoplastic films of polyethylene or polypropylene, or composite materials such as a film-coated nonwoven material. A preferred material for the present invention is the same polyethylene film used for the backsheet. It is joined to the flap connecting member 44 using means essentially the same as those used to join the attachment member 46 to the flap connecting member 44 described hereinabove.

Figure 5:
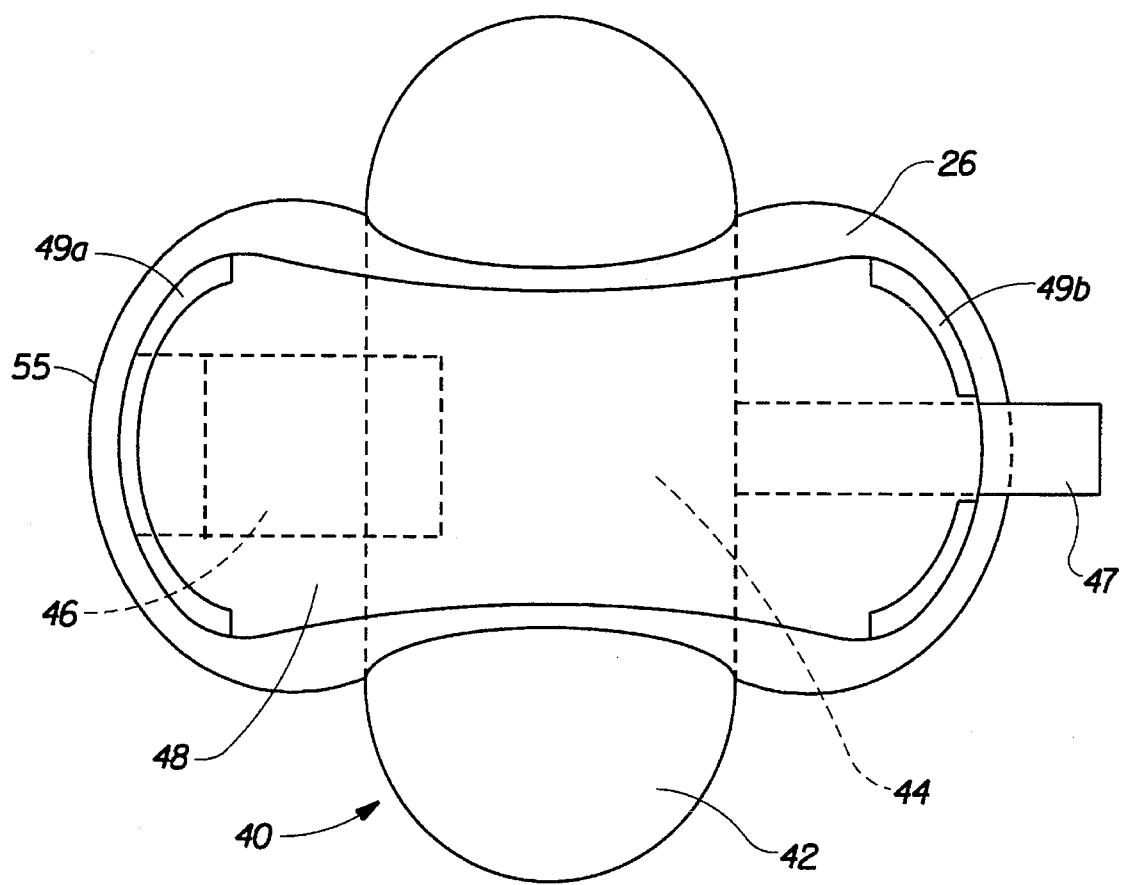
FIG. 5 is a plan view of the garment facing side of a sanitary napkin with the alternative embodiment of the adjustable undergarment protection system shown in FIG. 4 (some elements of the sanitary napkin that are shown in FIG. 4 are not shown in FIG. 5 for simplicity).

The relationship of the adjustment tab 47 to other elements of the adjustable protection system 40 is shown in FIGS. 4 and 5. Preferably, the adjustment tab 47 is joined to the transverse edge 54 of the flap connecting member 44 opposite that edge to which the attachment member 46 is joined. The adjustment tab 47 extends along the longitudinal centerline therefrom past the end edge 55 of the central absorbent body 20. The adjustment tab 47 is wide enough to provide a firm grasping surface for a wearer. In the most preferred embodiment the adjustment tab 47 extends roughly 12 mm (½ inch) in the transverse direction on each side of the longitudinal centerline 100. In other embodiments, two adjustment tabs 47 can be provided that are joined to each transverse edge 54 of the flap connecting member 44 replacing both attachment members 46.

As shown in FIGS. 4 and 5, the slip element 48 substantially covers the backsheet 26 and overlies the flap connecting member 44, the attachment member 46, and a large portion of the adjustment tab 47. Further, the slip element 48 has two transverse ends and each transverse end has a central portion and two side portions. The slip element 48 is shown in FIG. 4 as being unattached to the backsheet 26 along the central absorbent body longitudinal centerline 100 to allow the adjustment tab 47 to move freely in the longitudinal direction. This is also shown in FIG. 5, where attachment area 49b does not include the central portion of that transverse end of the slip element 48.

The slip element 48 can comprise any thin, flexible material. Examples include woven or nonwoven material, polymeric films such as thermoplastic films of polyethylene or polypropylene, or composite materials such as a film-coated nonwoven material. A preferred material for the present invention is the same polyethylene film used for the backsheet.

As is most clearly shown in FIG. 5, the slip element 48 is joined to the backsheet 26 adjacent to that end edge 55a which is adjacent the attachment member 46. It can be joined using any means familiar to the art. Preferably, the same means are used to join the slip element 48 to the backsheet 26 as are used to join the topsheet 24 to the backsheet 26. That is, a laterally continuous seal, traversing the full transverse width of the central absorbent body 20, is formed between one end of the slip element 48 and the backsheet 26 adjacent end edge 55a. This attachment area is identified as 49a in FIG. 5. That is, in attachment area 49a, the central portion and both side portions of one transverse end of slip element 48 are joined to the backsheet 26 adjacent end edge 55a. Side portions of the opposite end of the slip element 48 are joined to the backsheet 26 along the opposite transverse end 55b adjacent both longitudinal sides 50 of the central absorbent body 20. A central portion of the transverse end of that slip element, adjacent the longitudinal centerline 100 and slightly wider than the adjustment tab 47, is left unconnected. This attachment area is identified as 49b in FIG. 5. As shown in FIGS. 4 and 5, the adjustment tab 47 passes through the unconnected portion between the slip element 48 and the backsheet 26. The unconnected portion provides a channel between connected portions which limits the transverse motion of the adjustment tab 47 and allows the adjustment tab 47 to slide freely for adjusting the flaps 42. If two adjustment tabs 47 are provided, the slip element 48 is joined to the backsheet only along outside portions of both transverse ends of the central absorbent body 20. That is, the slip element 48 is joined to the backsheet 26 as in attachment area 49b. The pad adhesive 32 is disposed on the garment facing side of the slip element 48 for attaching the central absorbent body 20 to the crotch region of a wearer's undergarment.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary sanitary napkin for protecting an undergarment from soiling, said sanitary napkin having a longitudinal centerline, said sanitary napkin comprising:

a central absorbent body having a transverse centerline, longitudinal edges, and end edges, said central absorbent body comprising:
a liquid pervious topsheet;
a liquid impervious backsheet joined with said topsheet;
an absorbent core between said topsheet and said backsheet; and
means for attaching said central absorbent body to said undergarment disposed on said central absorbent body; and a longitudinally adjustable undergarment protection system joined to said central absorbent body, said adjustable undergarment protection system comprising:
a pair of flaps, said flaps extending transversely beyond said longitudinal edges of said central absorbent body and being longitudinally adjustable relative to said central absorbent body so that said flaps and said central absorbent body can be independently positioned in said undergarment;
at least one longitudinally extending attachment member joining said flaps and said central absorbent body, said attachment member comprising a longitudinally extensible component allowing longitudinal adjustment of said flaps relative to said transverse centerline of said central absorbent body; and
a means for attaching said flaps to said undergarment disposed on said flaps.

2. The sanitary napkin of claim 1 wherein said adjustable undergarment protection system further comprises
a flap connecting member having longitudinal sides and transverse ends, said flaps being joined to and transversely extending from each of said longitudinal sides of said flap connecting member and said flaps being indirectly joined to said central absorbent body through said flap connecting member.

3. A sanitary napkin according to claim 1 wherein said adjustable undergarment protection system further comprises attachment members joining each of said transverse ends of said flap connecting member to said backsheet.

4. A sanitary napkin according to claim 1 wherein the longitudinal adjustment index of said flaps is between about 5% and about 50%.

5. A sanitary napkin according to claim 2 wherein said longitudinally extensible component comprises at least two transversely oriented folds defining a pleat.

6. A sanitary napkin according to claim 2 wherein said longitudinally extensible component comprises slack in said attachment member.

7. A sanitary napkin according to claim 2 wherein said longitudinally extensible component comprises a material having a low yield value and a high elongation to break.

8. A unitary sanitary napkin for protecting an undergarment from soiling, said sanitary napkin having a longitudinal centerline, said sanitary napkin comprising:

- a central absorbent body having a transverse centerline, longitudinal edges, and end edges, said central absorbent body comprising:
  - a liquid pervious topsheet;
  - a liquid impervious backsheet joined with said topsheet;
  - an absorbent core between said topsheet and said backsheet; and
  - means for attaching said central absorbent body to said undergarment disposed on said central absorbent body; and
- a longitudinally adjustable undergarment protection system joined to said central absorbent body, said adjustable undergarment protection system comprising:
  - a pair of flaps, said flaps extending transversely beyond said longitudinal edges of said central absorbent body and being longitudinally adjustable relative to said central absorbent body so that said flaps and said central absorbent body can be independently positioned in said undergarment;
  - at least one longitudinally extending attachment member joining said flaps and said central absorbent body, said attachment member comprising a longitudinally extensible component allowing longitudinal adjustment of said flaps relative to said transverse centerline of said central absorbent body;
  - a flap connecting member having longitudinal sides and transverse ends, said flaps being joined to and transversely extending from each of said longitudinal sides of said flap connecting member and said flaps being indirectly joined to said central absorbent body through said flap connecting member;
- an adjustment tab, said adjustment tab being joined to and extending longitudinally from one of said transverse ends of said flap connecting member beyond one of said end edges of said central absorbent body; and
- a means for attaching said flaps to said undergarment disposed on said flaps.

\* \* \* \* \*